(12) United States Patent
Petcavich et al.

(10) Patent No.: US 9,568,497 B2
(45) Date of Patent: Feb. 14, 2017

(54) SCRATCH RESISTANT TOUCH SENSOR

(71) Applicant: UNIPIXEL DISPLAYS, INC., The Woodlands, TX (US)

(72) Inventors: Robert J. Petcavich, The Woodlands, TX (US); Danliang Jin, The Woodlands, TX (US)

(73) Assignee: UNIPIXEL DISPLAYS, INC., The Woodlands, TX (US)

( * ) Notice: Subject to any disclaimer, the term of this patent is extended or adjusted under 35 U.S.C. 154(b) by 0 days.

(21) Appl. No.: 14/354,526

(22) PCT Filed: Oct. 24, 2012

(86) PCT No.: PCT/US2012/061602
§ 371 (c)(1),
(2) Date: Apr. 25, 2014

(87) PCT Pub. No.: WO2013/063051
PCT Pub. Date: May 2, 2013

(65) Prior Publication Data
US 2014/0327452 A1 Nov. 6, 2014

Related U.S. Application Data

(60) Provisional application No. 61/551,030, filed on Oct. 25, 2011.

(51) Int. Cl.
*G01R 1/02* (2006.01)
*C12P 19/34* (2006.01)
(Continued)

(52) U.S. Cl.
CPC .............. *G01R 1/02* (2013.01); *C09D 133/04* (2013.01); *C12N 9/78* (2013.01); *C12N 15/102* (2013.01);
(Continued)

(58) Field of Classification Search
CPC ... G01R 27/2605; G06F 3/044; H03K 17/955; G01B 7/003; G01D 5/24
(Continued)

(56) References Cited

U.S. PATENT DOCUMENTS 3,998,715 A * 12/1976 Bohm .................. C08F 259/04
522/121
4,291,656 A 9/1981 Miyagi et al.
(Continued)

FOREIGN PATENT DOCUMENTS

CN 1446371 A 10/2003
CN 1711486 A 12/2005
(Continued)

OTHER PUBLICATIONS

Office Action mailed May 12, 2015, Japanese Patent Application No. 2014-538909, 4 p.
(Continued)

*Primary Examiner* — Jermele M Hollington
*Assistant Examiner* — Christopher McAndrew
(74) *Attorney, Agent, or Firm* — Nixon Peabody LLP; Joseph Bach, Esq.

(57) ABSTRACT

A method of manufacturing a scratch resistant, touch sensor comprising: (1) applying a non-polymer protective coating solution to a touch sensor; and (2) forming a cross-linked polymer structure by curing the protective coating solution.

9 Claims, 11 Drawing Sheets

(51) Int. Cl.
  *C12N 9/78* (2006.01)
  *C12N 15/10* (2006.01)
  *C09D 133/04* (2006.01)
  *G01R 27/26* (2006.01)
  *G01B 7/00* (2006.01)
  *G01D 5/24* (2006.01)

(52) U.S. Cl.
  CPC .............. *C12P 19/34* (2013.01); *G01B 7/003* (2013.01); *G01D 5/24* (2013.01); *G01R 27/2605* (2013.01); *Y02P 20/52* (2015.11)

(58) Field of Classification Search
  USPC ........................................................ 324/658
  See application file for complete search history.

(56) References Cited

U.S. PATENT DOCUMENTS

| | | | |
|---|---|---|---|
| 6,308,619 B1 | 10/2001 | Dawley | |
| 6,406,758 B1* | 6/2002 | Bottari | G06F 3/041 427/162 |
| 6,660,397 B2* | 12/2003 | Fitch | C08J 7/047 428/328 |
| 7,291,656 B2 | 11/2007 | Bulluck et al. | |
| 7,728,075 B2* | 6/2010 | Schellekens | C08F 8/30 525/124 |
| 9,248,468 B2 | 2/2016 | Bulluck | |
| 2002/0127330 A1 | 9/2002 | Jin et al. | |
| 2002/0137872 A1 | 9/2002 | Schneider et al. | |
| 2002/0160205 A1 | 10/2002 | Garcia et al. | |
| 2003/0154871 A1 | 8/2003 | Laksin et al. | |
| 2008/0174140 A1 | 7/2008 | McCormick et al. | |
| 2009/0153504 A1* | 6/2009 | Liu | G06F 3/045 345/173 |
| 2009/0274914 A1 | 11/2009 | Hoshi et al. | |
| 2009/0303602 A1* | 12/2009 | Bright | G02B 1/111 359/585 |
| 2010/0233596 A1* | 9/2010 | Ikeda | C07C 333/04 430/7 |
| 2011/0159249 A1 | 6/2011 | Choi | |
| 2011/0189477 A1* | 8/2011 | Miracle | B32B 7/06 428/349 |
| 2011/0204281 A1* | 8/2011 | Rouse | B82Y 30/00 252/75 |
| 2011/0254908 A1* | 10/2011 | Sturme | B41M 5/502 347/88 |

FOREIGN PATENT DOCUMENTS

| | | |
|---|---|---|
| CN | 1305920 C | 3/2007 |
| CN | 201210288 Y | 3/2009 |
| CN | 201369033 Y | 12/2009 |
| JP | 09-230985 | 5/1997 |
| JP | 2004344873 A | 12/2004 |
| JP | 2010-257350 | 11/2010 |
| JP | 2011-175967 | 8/2011 |
| JP | 2011-192150 | 9/2011 |
| JP | 2011-198698 | 10/2011 |
| TW | 200738463 A | 10/2007 |
| TW | 200825043 A | 6/2008 |
| TW | 200914551 A | 4/2009 |
| WO | 2009/079572 A1 | 6/2009 |

OTHER PUBLICATIONS

PCT/US2012/061602 International Search Report and Written Opinion dated Feb. 28, 2013 (12 pgs.).
Jeonghun, Kim, et al., "Flexible Conductive Polymer Patterns from Photo Cross-linkable DOT and Their Electrochromic Display Application", Department of Chemical and Biomolecular Engineering, Yonsei University, vol. 14, pp. 17-20, Oct. 2010.
Unknown Cited Article dated Sep. 30, 2010.
Office Action for Chinese Patent Application No. 201280058274.5 dated Jan. 26, 2016.
Office Action for Chinese Patent Application No. 201280058273.0 dated Mar. 1, 2016.
Office Action for U.S. Appl. No. 14/727,843 dated Apr. 13, 2016.
Examination Report for Taiwanese Patent Application No. 101121704 dated Aug. 3, 2016.
Examination Report for Taiwanese Patent Application No. 101139207 dated Jul. 29, 2016.
Office Action for U.S. Appl. No. 14/727,789 dated Oct. 7, 2016.
Office Action for U.S. Appl. No. 14/727,818 dated Oct. 6, 2016.
Restriction Requirement for U.S. Appl. No. 14/354,507 dated Oct. 26, 2016.
Second Office Action for Chinese Patent Application No. 201280058274.5 dated Oct. 8, 2016.
International Preliminary Report on Patentability for PCT/US2015/033619 dated Nov. 3, 2016.
International Preliminary Report on Patentability for PCT/US2015/033623 dated Nov. 3, 2016.
Office Action for U.S. Appl. No. 14/727,843 dated Nov. 10, 2016.
International Preliminary Report on Patentability for PCT/US2015/033631 dated Nov. 3, 2016.

* cited by examiner

SCRATCH RESISTANT TOUCH SENSOR

CROSS-REFERENCE TO RELATED APPLICATION

This application is a national stage of and claims priority under 35 U.S.C. §371 to International Patent Application Serial No. PCT/US2012/061602, filed on Oct. 24, 2012, entitled "SCRATCH RESISTANT TOUCH SENSOR" by Robert PETCAVICH, et al., which claims the benefit of and priority under 35 U.S.C. §119 to U.S. Provisional Patent Application No. 61/551,030, filed on Oct. 25, 2011, "TOUCH SENSOR PATTERNED ELECTRODES WITH SCRATCH RESISTANCE LAYER" by Robert PETCAVICH, et al., both of which are incorporated herein by reference in their entirety for all purposes.

BACKGROUND

Touch screen technology has become an important component of many modern electronics, such as tablet computers and cellular phones. Typically, touch screen technology incorporates the use of resistive or capacitive sensor layers which make up part of the display. Screens for devices which utilize such technology are often prone to damage due to the increased level of direct contact by the user with the screen. Such damage typically includes both scratching and breakage of the screen itself depending on the materials used and the use thereof. As a result, resistive and capacitive touch sensors usually include translucent electrical insulating covers placed on top of the display structure in order to protect and isolate the touch sensor panel from environmental conditions, abrasion, oxygen, and harmful chemical agents.

Resistive and capacitive touch screen technologies require materials that are both transparent and conductive to be functional. Indium Tin Oxide (ITO) is currently the most widely used metal oxide for touch screen sensor applications because it is optically transparent and is has fair conductive properties. ITO is commonly employed to make transparent conductive coatings for liquid crystal displays, flat panel displays, touch panels, solar panels and aircraft windshields. In resistive touch screens, when a user touches the screen with a finger or a stylus, the ITO film is pushed into contact with the ITO glass producing a voltage signal allowing a processor to compute the coordinates of the touch event and process the appropriate response to the touch point. Although the use of ITO is a well-known and accepted technology, it is not ideal. The main issues with ITO are the limited supply and the rising cost of indium, in addition to its fragility, lack of flexibility and low conductivity compared to other metals.

As previously stated, it is typical to employ glass or polyester layers as protective covers in touch screen panels. Polyester films, while flexible, can only provide a minimal level of hardness. Specifically, such films provide a surface harness ranging from about 2H to 4H. As a result, polyester films are susceptible to scratches. On the other hand, glass covers, which are able to produce pencil hardness readings above 7H, do provide very good scratch protection. However, such glass covers do not provide a high level of flexibility and are therefore susceptible to breaking upon impact with a hard surface.

SUMMARY

The present disclosure relates to a scratch resistant, touch sensor, comprising a transparent, dielectric substrate, a first conductive layer formed on a first side of the substrate, a second conductive layer formed on a second side of the substrate, and a scratch resistant, protective coating applied to at least one of the first and second conductive layers, said coating comprising a cross-linked polymer structure.

Other embodiments are directed to a method of manufacturing a scratch resistant, touch sensor comprising: (1) applying a protective coating solution to a touch sensor; and (2) forming a cross-linked polymer structure by curing the protective coating solution.

BRIEF DESCRIPTION OF THE DRAWINGS

For a detailed description of exemplary embodiments of the invention, reference will now be made to the accompanying drawings in which.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

As used herein, the word "approximately" means "plus or minus 10%." Additionally, as used herein, the word "transparent" means any material that's allows the transmission of light waves within a transmittance rate of 90% or greater.

Figure 1:
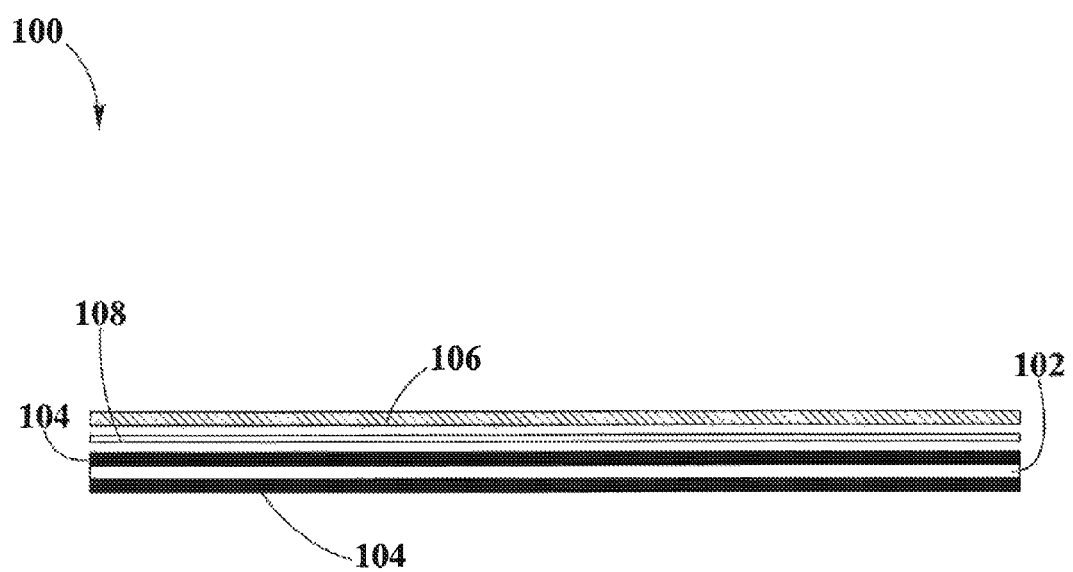
FIG. 1 shows a cross-sectional representation of a typical capacitive touch screen.

FIG. 1 shows a cross-sectional representation of a typical capacitive touch screen 100. Touch screen 100, comprises a transparent dielectric substrate 102 that is coated on both sides with two layers of a transparent, conductive material 104. In a typical arrangement, transparent, conductive material 104 is composed of ITO, however the transparent, conductive material 104 may also be composed of conductive plastic, silver (Ag), gold (Au), aluminum alloys, and other materials.

A top transparent, electrically insulating cover 106 is adhered to the top layer of transparent conductive material 104, by means of a transparent, electrically insulating adhesive 108. Examples of suitable materials for the transparent and electrically insulating cover 106 include polyester film, glass, and polycarbonate plastic. Additionally, an example of a suitable transparent, electrically insulating adhesive 108 is 3M #8142.

Figure 2:
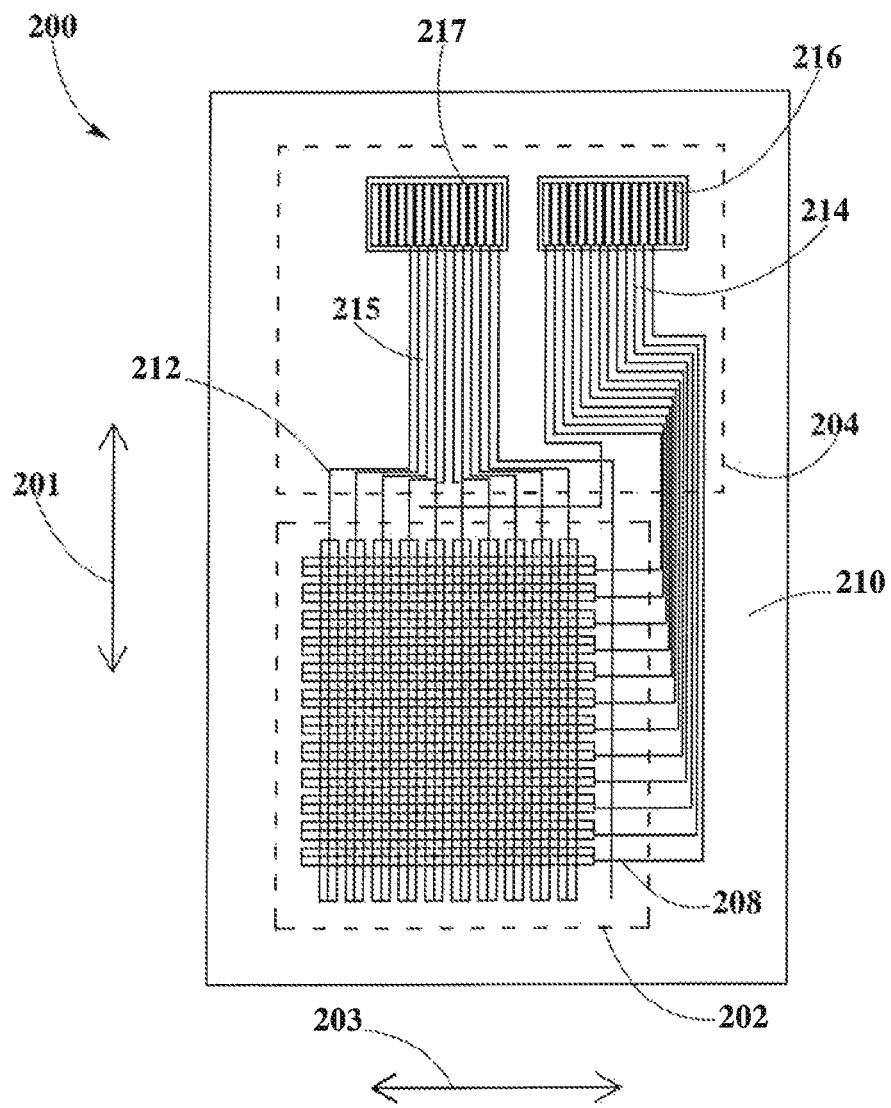
FIG. 2 shows a top view of an alternative capacity touch sensor screen.

Referring now to FIG. 2, a top view of a capacity touch sensor screen 200 in accordance with the preferred embodiment is shown. Screen 200 generally comprises a thin, flexible, transparent, dielectric substrate 210, a horizontal axis 203, a vertical axis 201, a transparent, electrically conductive, capacitive grid 202, and a transparent, electrically conductive, capacitive tail 204.

Figure 3:
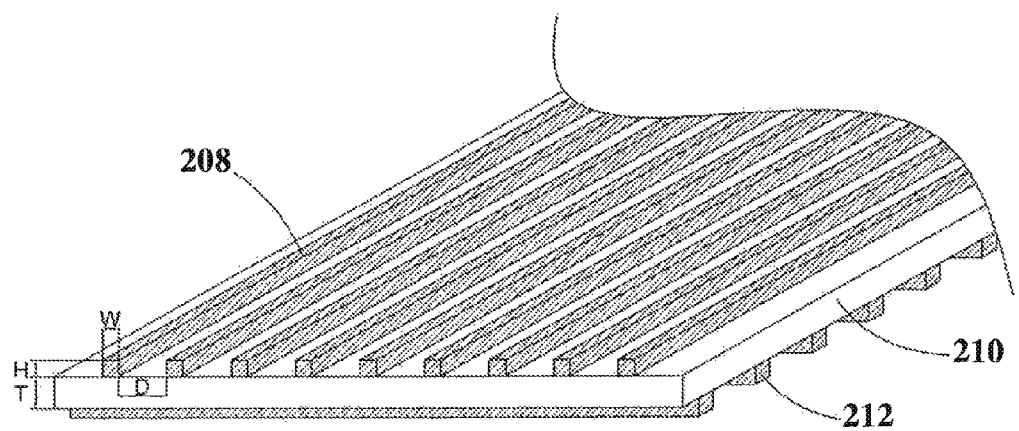
FIG. 3 shows an isometric view of the capacity touch sensor screen shown in FIG. 2.

As is best shown in FIGS. 2 and 3, grid 202 is further comprised of a first plurality of conductive lines 208 extending in a direction parallel to the horizontal axis 203 and on one side of the dielectric substrate 210. A second plurality of conductive lines 212 extend in a direction parallel to the vertical axis 201 and on the opposing side of the dielectric substrate 210. The first plurality of conductive lines 208 and second plurality of conductive lines 212 are isolated by the dielectric substrate 210 and form grid 202 that, in turn, enables the recognition of a point of user interaction with the screen. An example of conductive capacitive grid 202 may comprise a 9×16 array of conductive lines or more, with a surface area ranging from about 2.5×2.5 mm to 2.1×2.1 m.

Grid 202 may also operate under a mutual capacitance principle, whereby grid 202 forms a capacitor at each intersection of each of the first plurality of conductive lines 208 and each of the second plurality of conductive lines 212. For example, a 9-by-16 array would have 144 independent capacitors. A voltage is then applied to the first plurality of conductive lines 208 and the second plurality of conductive lines 212, such that bringing a finger or conductive stylus near the surface of the sensor changes the local electric field which reduces the mutual capacitance. The capacitance change at every individual point on the grid can be measured to accurately determine the touch location by measuring the voltage in both the horizontal axis 203 and the vertical axis 201. As a result, mutual capacitance may allow multi-touch operation where multiple fingers, palms, or styluses can be accurately tracked at the same time.

Referring back to FIG. 2, tail 204 comprises electrical leads 214 and electrical connectors 216 that are disposed on one side of the dielectric substrate 210 and connect with the first plurality of conductive lines 208. Similarly, tail 204 also comprises electrical leads 215 and electrical connectors 217 that are disposed on the opposing side of the dielectric substrate 210 and connect with the second plurality of conductive lines 212.

In some embodiments, the first plurality of conductive lines 208, the second plurality of conductive lines 212, electrical leads 214, electrical connectors 216, electrical leads 215, and electrical connectors 217 of screen 200 may be comprised of copper, silver, gold, nickel, tin, palladium, and conductive polymers. Additionally, in some embodiments, dielectric substrate 210 may comprise polyethylene terephthalate (PET) film, metal, paper, or glass. Specifically, suitable materials for substrate 204 may include DuPont/Teijin Melinex 454 and Dupont/Teijin Melinex ST505, the latter being a heat stabilized film specially designed for processes where heat treatment is involved.

Most protective coatings applied in touch screen devices exhibit a polymer-based molecular structure. Polymers are relatively large molecules which result from chemically linking thousands of relatively small molecules called monomers. Monomers, due to their weak intermolecular forces, can exist in the form of gases, liquids, or structurally weak molecular structures.

Figure 4:
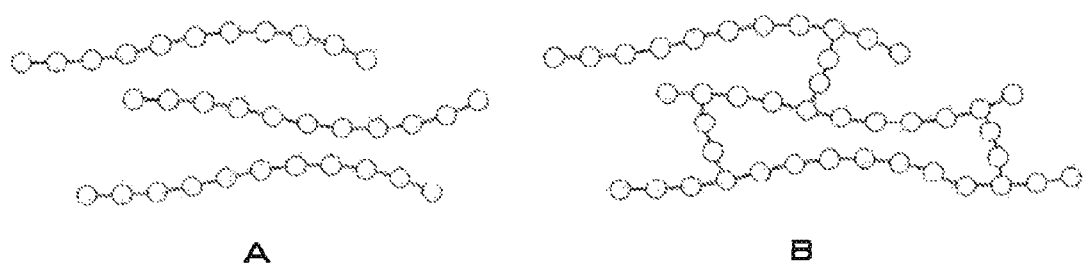
FIG. 4 shows both a linear polymer structure (A) as well as a cross-linked polymer structure (B) in accordance with an embodiment of the invention.

FIG. 4 shows an example of a linear polymer structure A and a cross-linked polymer structure B. As used herein, the term "Cross-Linked" refers to chemical bonds (covalent or ionic) that link one monomer or polymer chain to another. In a typical polymerization reaction, monomers with dual functional groups are joined together to form polymers in a linear polymer structure A. However, screens made with a polymer-based coating containing linear polymer structure A, are not usually scratch resistant. Therefore, in order to increase the scratch resistance of the coating film, the mechanical strength of the polymeric coating needs to be enhanced.

Cross-linked polymer structures B are linked together in a three dimensional structure that increases the intermolecular forces (usually covalent bonds) within the polymer chains and reduces the polymeric chain relaxation that usually manifests as a dent or gouge under pressure. Therefore, polymer-based coating films which contain cross-linked polymer structures B, will tend to have scratch resistant properties.

Although the molecular strength is higher for a cross-linked polymer structure, application or coating of the polymer onto a substrate or screen may not be possible through a solution process. This is due to the fact that cross-linked polymers cannot dissolve in any solvent and can only swell when placed therein. Coating compositions normally need to be in a liquid state to allow molecules to move and react more efficiently. Materials with low density, cross-linked materials behave as viscous, liquid-like gels, while materials with high density cross-linked networks are very rigid in their solid state. Therefore, in order to achieve a cross-linked structure after it is applied to a substrate or screen in a liquid form, it is necessary to form a cross-linked structure after the coating is applied.

Embodiments of the current invention employ a scratch resistant, protective coating based on a cross-linked structure that does not originate from a polymer chain. Instead, the coating may be comprised of monomers that react simultaneously at different joint points to create a cross-linked, three dimensional polymer structure that exhibits very high cross-linked densities, and hence, scratch resistant features. Specifically, the transparent, scratch resistant coating may comprise mono and multifunctional acrylic monomers and oligomers. This coating may be applied over a touch sensor screen protecting the screen from environmental conditions, chemicals, wear, abrasion, scratches, thereby eliminating the need to use an extra insolating glass or PET cover 106 as shown in FIG. 1.

Figure 5:
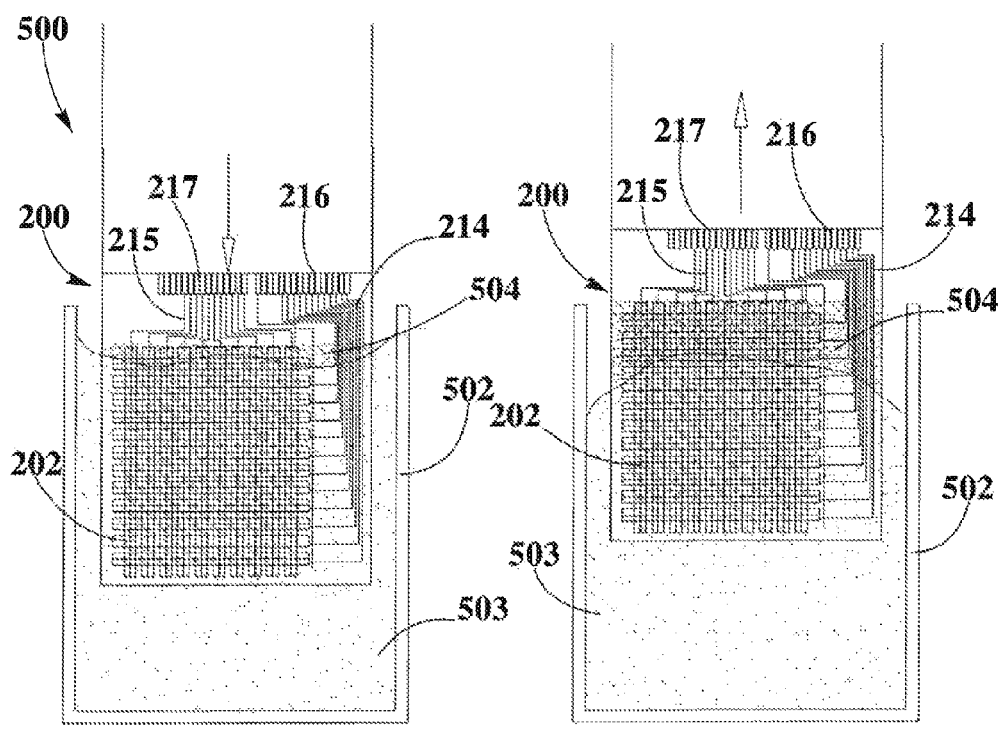
FIG. 5 depicts a schematic view of a coating application system for applying a transparent, scratch resistant coating in accordance with an embodiment of the invention.

Referring now to FIG. 5, a coating application system 500 is shown for applying a transparent, scratch resistant coating 504 to a touch sensor screen 200 is shown. Coating application system 500 generally includes a vessel 502 that further contains a transparent coating solution 503 in a liquid state. In order to apply the protective coating 504 to screen 200, screen 200 may be immersed in the coating solution 503 contained in the vessel 502 and then withdrawn at a constant speed and temperature to avoid any jitters. In some embodiments, only the grid 202 requires protective coating 504 since it is the area that the user will interact with. Accordingly, the electrical leads 214, 215 and electrical connectors 216, 217 may not require protection since the user is not interacting with them. However, in other embodiments, the scratch resistant coating 504 may be applied to at least a portion of the electrical leads 214, 215 and electrical connectors 216, 217.

Figure 7:
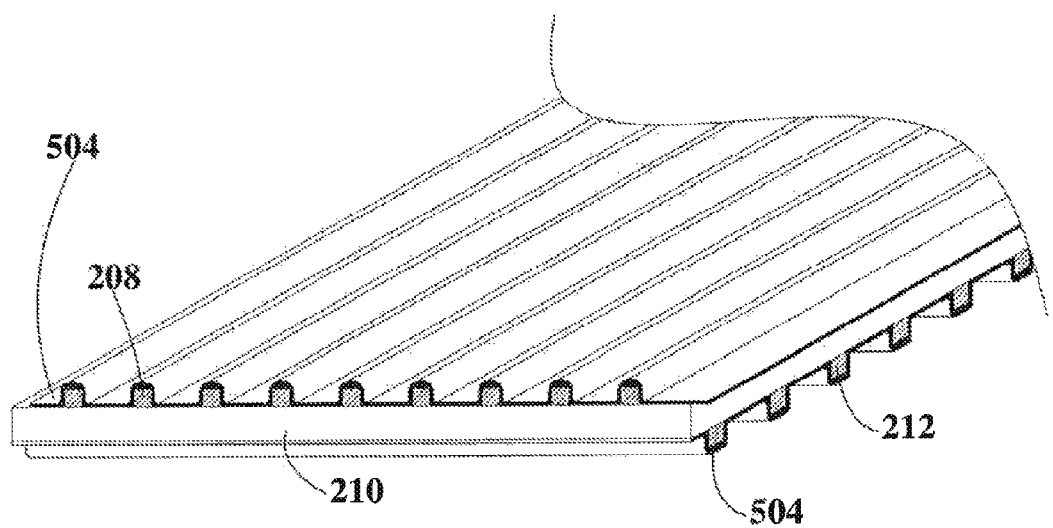
FIG. 7 shows an isometric view of a touch sensor screen with a transparent, scratch resistant coating in accordance with an embodiment of the invention.

Referring briefly to FIG. 7, an isometric view of the combination of screen 200 and coating 504 is shown after passing through the coating application system 500 described in FIG. 5 above.

Referring again to FIG. 5, the thickness of the scratch resistant coating 504 may be defined, at least in part, by the withdrawal speed of the screen 200 from the vessel 502. More specifically, a faster withdrawal speed pulls more fluid up onto the surface of the screen 200 before it has time to flow back down into the vessel 502. Withdrawal speed may vary in some embodiments from about 1 in/min to 1 ft/min, while thickness may range from about 5 to 50 microns with 20 microns being preferred. Other factors that may affect the thickness of the scratch resistant coating 504 may include the viscosity, density, volatility of solvents used, and solid content of the coating solution 503. In some embodiments, the scratch resistant coating 504 exhibits a combination of 70% to 80% solid content with a photo-initiator concentration in the range of about 1% to about 6%, and about 20% to 30% solvent to regulate viscosity. The addition of solvent into the coating solution 503 does not affect the properties of scratch resistant coating 504 because it evaporates after application.

Figure 6:
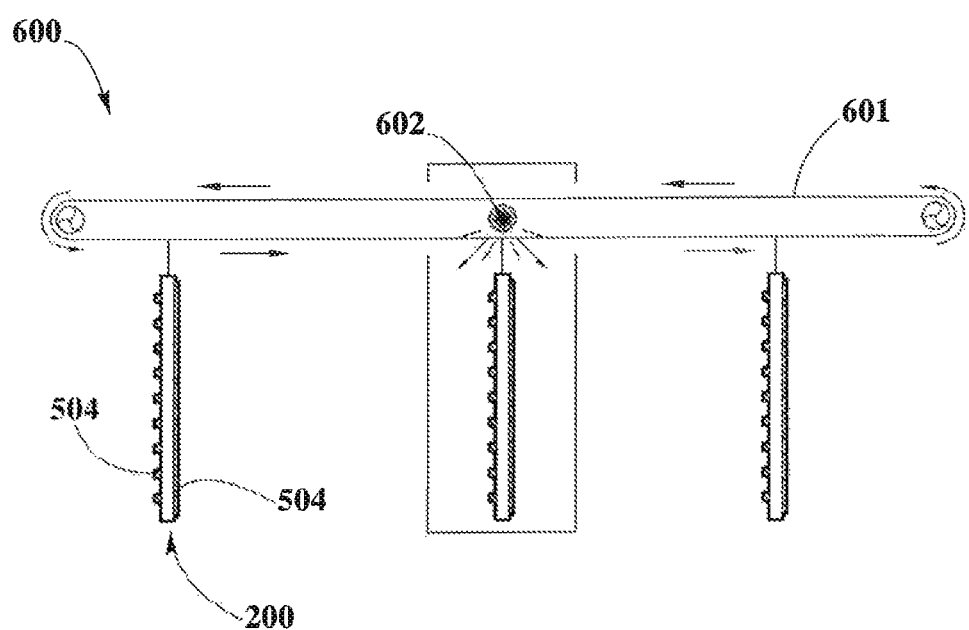
FIG. 6 shows a curing process in accordance with an embodiment of the invention.

Referring now to FIG. 6, after transparent, scratch resistant coating 504 is applied to screen 200 via the coating application system 500 (FIG. 5), the coating 504 is cured via a curing process 600. Curing process 600 generally includes a conveyor 601, and an ultraviolet (UV) light source 602. During operation, the combination of screen 200 and coating 504 is moved along conveyor 601, such that UV light source 602 cures coating 504 as it passes by. In some embodiments, UV light source 602 is an industrial grade UVA light source which will enable coating 504 to cure in a very short period of time. Specifically, curing may take place on the order of about 0.1 to 2.0 seconds. Additionally, in some embodiments, UV light source 602 has a wavelength of about 280 to 480 nm, with target intensity in the range of 0.5 to 20.0 J/cm². Furthermore, in order to achieve higher levels of cross link density, the UV light curing process described above should be carried out in an inert gas environment or in an environment substantially free of oxygen. An example of a suitable inert gas for this process is nitrogen.

In other embodiments, curing of the scratch resistant coating 504 is accomplished by means of a thermo-curing process. During a thermo-curing process the combination of screen 200 and coating 504 goes through a line conveyor within a thermal oven whereby heat radiation is applied to cure the scratch resistant coating 504 and allow the formation of a cross-linked polymer structure therein. Heat radiation applied on the scratch resistant coating 504 may range in temperatures from about 70° C. to 100° C. for a time period of approximately 5 to 300 seconds. Furthermore, in order to achieve higher levels of cross link density, the thermo-curing process described above should be carried out in an inert gas environment or in an environment substantially free of oxygen. An example of a suitable inert gas for this process is nitrogen or carbon dioxide.

In still other embodiments, curing of the scratch resistant coating 504 is accomplished by means of applying ionizing radiation to the coating 504. For example, in the embodiment shown, an electronic beam (E-beam) curing process is used to cure the coating 504. An E-beam curing process applies an electron discharge 404 to cure the scratch resistant coating. More specifically, an E-beam curing process utilizes highly energetic electrons at controlled doses to quickly polymerize and cross-link polymeric materials. There is no need to use either a thermo or photo initiator within transparent, scratch resistant coating 504 when employing an E-Beam curing process, because the electrons within the solution act as the initiator. E-beam doses applied to the scratch resistant coating 504 may range from about 0.5 to 5.0 MRads. As with other curing methods, in order to achieve higher levels of cross link density, the E-beam curing process described above should be carried out in an inert gas environment or in an environment substantially free of oxygen. An example of a suitable inert gas for this process is nitrogen.

Crosslinking density refers to the percentage of cross-linked bonds within a given polymer. Such density is related to reaction time and temperature. Generally, a higher intensity and faster reaction translates into a higher cross-linked density. Cross-link density for coating 504 may range from about 60% to 70% for a UV curing process (EX: the coating application system 500 shown in FIG. 6), 50% to 60% for a thermo-curing process, and up to 80% for an E-beam curing process. In light of the foregoing, a UV curing process is an effective curing method from a manufacturing perspective when one considers processing speed, cost, and power requirements.

Figure 8:
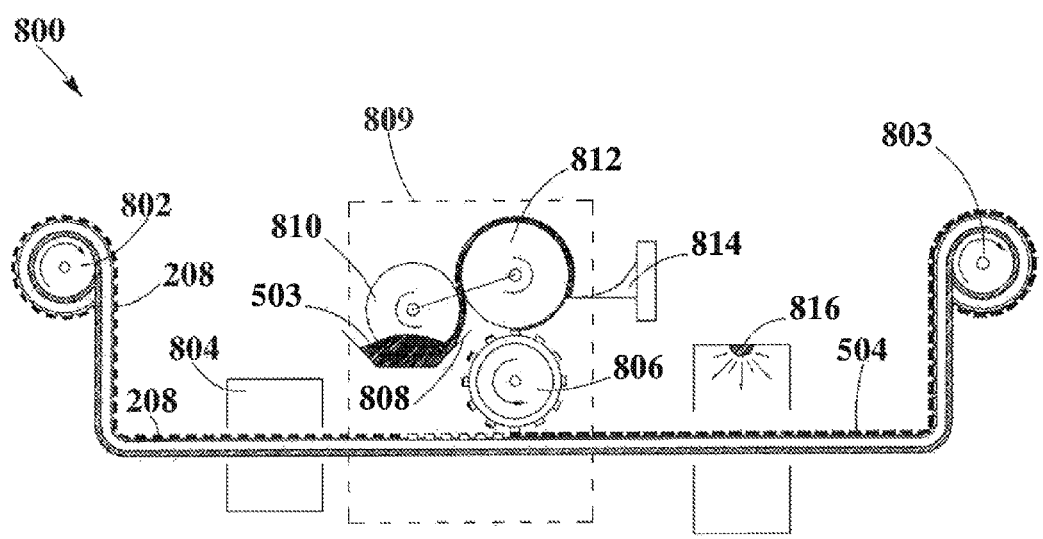
FIG. 8 depicts a schematic view of an alternative embodiment of a coating application for applying a transparent, scratch resistant coating in accordance with an embodiment of the invention.

Referring now to FIG. 8, an alternative embodiment of a coating application system 800 is shown. Whereas coating application system 500 (FIG. 5) employs a dip coating method, the alternative coating application system 800 applies coating solution 504 to the first plurality of conductive lines 208 using a flexographic or gravure printing process. Coating application system generally comprises an unwind roll 802, a web cleaner 804, a flexographic printing module 809, a UV light source 816, and a wind-up roll 803. During operation, screen 200 is unrolled from unwind roll 802, passes through web cleaner 804 where dust particles and impurities are removed, and enters into flexographic printing module 809 where coating 504 is deposited on the surface of screen 200. The combination of screen 200 and coating 504 then moves past UV light source 816 where coating 504 is cured and a cross-linked polymeric structure is formed, as is described above. Finally, the combination of screen 200 and coating 504 is deposited on windup roll 803. The above mentioned steps and modules will be described in more detail below.

Flexographic printing module 809 generally includes a coating pan 808, a transfer roll 810, an anilox roll 812, a doctor blade 814, and a master plate 806. Coating pan 808 contains an amount of coating solution 503 and is positioned such that some portion of the coating solution 503 contained in coating pan 808 is deposited onto transfer roll 810 as it rotates on a fixed axis. Coating solution 503 is then transferred from transfer roll 810 to anolix roll 812 at a point where anilox roll 812 contacts transfer roll 810. In some embodiments, anilox roll 812 is constructed of a steel or aluminum core and its outer surface is covered by an industrial ceramic whose surface contains a large number of very fine dimples referred to as cells.

Figure 9:
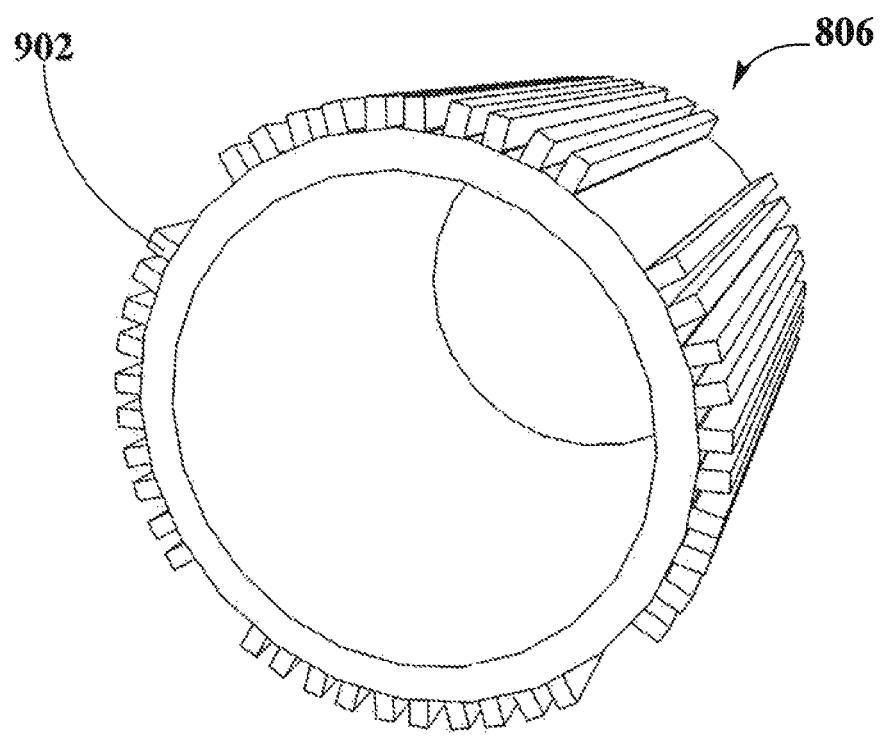
FIG. 9 shows an isometric view of an embodiment of a master roll in accordance with an embodiment of the invention.

Excess coating is then scraped away by means of the doctor blade 814. Doctor blade 814 is placed in a fixed location such that only a specifically desired amount of coating solution 503 remains on anilox roll 812 after the excess is scraped away. The measured amount of coating solution 503 is then deposited onto master roll 806 which rotates around such that coating solution 503 is deposited on the surface of screen 200. Master roll 810 has a printing pattern 902 distributed along its outer surface that may match the orientation of the first plurality of conductive lines 208, disposed of on screen 200 such that coating solution 503 may be distributed only on areas of screen 200 in which a user will interact. In other embodiments, coating solution 503 will be uniformly printed along the entire surface of screen 200. Referring briefly to FIG. 9, an isometric view of an embodiment of master roll 806 is shown such that printing pattern 902 presented in greater detail. Referring back to FIG. 8, once the combination of screen 200 and coating 504 leaves flexographic printing module 809, it moves toward UV light source 816 such that coating solution 504 is cured in the same manner as is described above.

Figure 10:
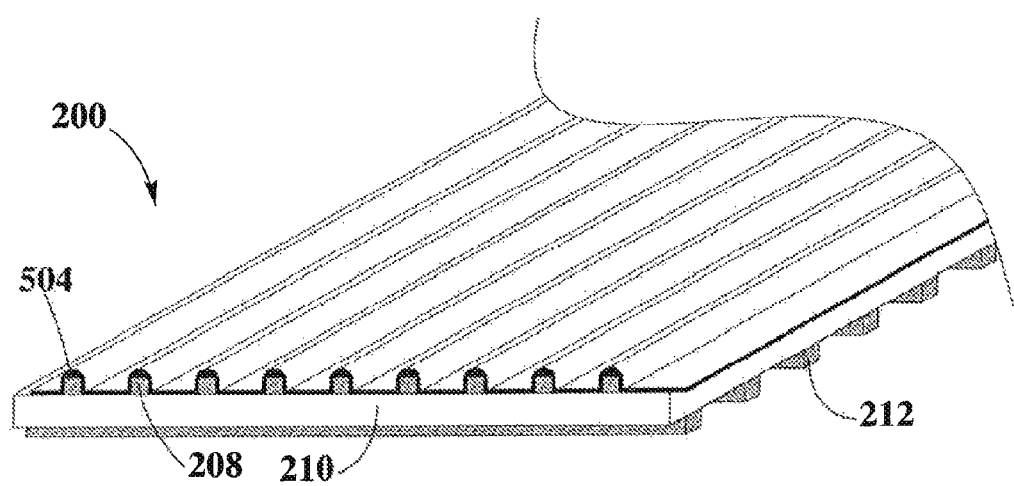
FIG. 10 shows an isometric view of alternative embodiment of a touch sensor screen with a transparent, scratch resistant coating in accordance with an embodiment of the invention.

Referring to FIG. 10, an isometric representation of the combination of screen 200 and coating 504 is shown after passing through the coating application system 800 described in FIG. 8 above.

Figure 11:
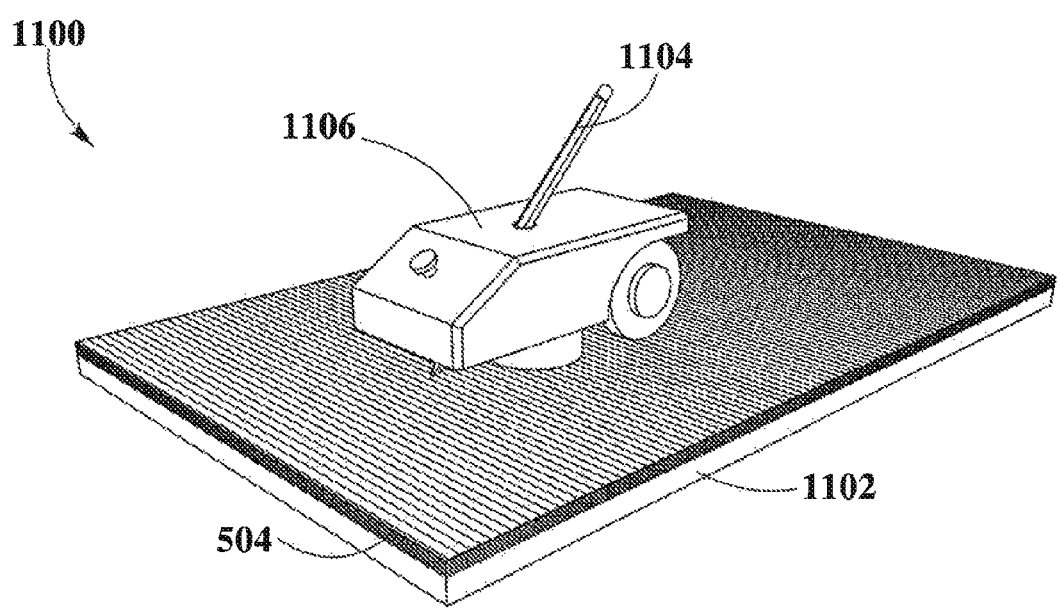
FIG. 11 shows the apparatus for conducting a pencil hardness test on the surface of the scratch resistant screen.

Referring now to FIG. 11, a pencil hardness test 1100, which complies with test method ASTM D3363, for measuring the surface hardness of coating 504, is shown. To perform the test, a pencil 1104 is selected from set of pencils that exhibit hardness ranging from 6B to 9H. Selecting from highest to lowest hardness, a first pencil 1104 is loaded into the measuring cart 1106. The measuring cart 1106 used in this test is the Elcometer 3080 which is commercially available from BAMR. This measuring instrument enables pencil 1104 to be maintained at a constant pressure force of about 7.5 N, and at the appropriate angle, which increases the reproducibility of the test. With pencil 1104 loaded, measuring cart 1106 is moved across the surface of coating 504. If the pencil 1104 leaves a scratch, the next softer pencil 1104 is used and the process is repeated. The hardness number of the first pencil 1104 that does not leave a scratch is considered the pencil hardness of coating 504.

Using thicknesses from about 5 to 50 microns, pencil hardness of coating 504 on top of the substrate film 1102 that is made of PET is measured from 2H up to 8H. Performance characteristics of coating 202 that is applied to a PET substrate 204 are shown in Table 1.

TABLE 1

| CATEGORY | SPECIFICATION | CHARACTERISTICS |
| --- | --- | --- |
| Optical Performance | Transmittance | >93% |
|  | Haze | <1% |
|  | Gloss | 20° = 95, 60° = 97, 85° = 99 |
|  | Brightness Loss | <1.7% optical loss when on display |
|  | Index of Refraction | 1.48-1.54 |
| Scratch Resistance | Hardness | 2H-8H |
| Thermal Stress | Operating Temperature | −20° C. to 65° C., 90 Cycles |
| | Storage Temperature | −40° C. for 72 hrs, 85° C. for 10 hrs |
| Chemical | Chemical Resistance | Exposure* for 1 hour @ 70° F. |

*IPA, acetone, glass cleaner, vinegar, coffee, tea, cola, ketchup, mustard

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method of manufacturing a flexible scratch resistant, touch sensor, comprising:
    forming a first plurality of conductive lines on a first surface of a heat stabilized substrate;
    forming a second plurality of conductive lines, oriented orthogonal to the first plurality of conductive lines, on an opposite surface of the heat stabilized substrate;
    forming a tail comprising a first set of leads and connectors connecting with the first plurality of conductive lines, and a second set of leads and connectors connecting with the second plurality of conductive lines;
    preparing a protective coating solution by mixing 70%-80% of multifunctional acrylic oligomers, 20%-30% solvent, and 1%-6% photoinitiators;
    applying the protective coating solution over the first surface and the opposite surface of the heat stabilized substrate to thereby coat the first and second plurality of conductive lines; and
    forming a cross-linked polymer structure by curing the protective coating solution.

2. The method of claim 1 wherein curing the protective coating solution is conducted in an environment of an inert gas.

3. The method of claim 1 wherein forming the cross-linked polymer structure achieves a cross-link density of 50% or higher.

4. The method of claim 1 wherein applying the protective coating solution comprises dipping the touch sensor into a vessel containing the protective coating solution.

5. The method of claim 1 wherein applying the protective coating solution comprises a flexographic printing process.

6. The method of claim 1 wherein applying the protective coating solution comprises either a slot-die or Gravure coating technique.

7. The method claim 1 wherein curing the protective coating solution comprises applying a UV light source having a wavelength from 280 to 480 nm at an intensity density of 0.5-20.0 J/cm$^2$.

8. The method of claim 1 wherein curing the protective coating solution comprises applying ionizing radiation to the protective coating solution.

9. The method of claim 8 wherein applying the ionizing radiation comprises applying doses of electrons ranging from 0.5 to 5 MRads.

* * * * *